United States Patent
Lee et al.

(10) Patent No.: US 10,169,641 B2
(45) Date of Patent: Jan. 1, 2019

(54) APPARATUS AND METHOD FOR VISUALIZATION OF REGION OF INTEREST

(71) Applicant: Samsung Electronics Co., Ltd., Suwon-si (KR)

(72) Inventors: Ki Yong Lee, Suwon-si (KR); Won Sik Kim, Gunpo-si (KR); Yeong Kyeong Seong, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 112 days.

(21) Appl. No.: 14/818,913

(22) Filed: Aug. 5, 2015

(65) Prior Publication Data
US 2016/0042525 A1 Feb. 11, 2016

(30) Foreign Application Priority Data
Aug. 5, 2014 (KR) .................. 10-2014-0100677

(51) Int. Cl.
| | |
|---|---|
| *G06K 9/00* | (2006.01) |
| *G06F 19/00* | (2018.01) |
| *A61B 8/00* | (2006.01) |
| *A61B 8/08* | (2006.01) |
| *G06K 9/20* | (2006.01) |

(52) U.S. Cl.
CPC .......... *G06K 9/00208* (2013.01); *A61B 8/469* (2013.01); *A61B 8/5223* (2013.01); *G06F 19/321* (2013.01); *G06K 9/2081* (2013.01); *A61B 8/08* (2013.01); *A61B 8/085* (2013.01); *A61B 8/0866* (2013.01); *G06K 2209/051* (2013.01)

(58) Field of Classification Search
None
See application file for complete search history.

(56) References Cited

U.S. PATENT DOCUMENTS

| | | | |
|---|---|---|---|
| 6,589,176 B2 | 7/2003 | Jago et al. | |
| 7,633,501 B2 | 12/2009 | Wood et al. | |
| 8,345,101 B2 | 1/2013 | Bobbitt et al. | |
| 8,475,382 B2 * | 7/2013 | Miyama | A61B 8/06 600/437 |
| 8,570,359 B2 | 10/2013 | Ali et al. | |
| 8,630,467 B2 * | 1/2014 | Masumoto | G06F 19/321 382/128 |
| 8,687,078 B2 | 4/2014 | Bigioi et al. | |
| 9,173,630 B2 * | 11/2015 | Kanda | A61B 8/08 |
| 2004/0143189 A1 * | 7/2004 | Lysyansky | A61B 8/08 600/450 |
| 2005/0113961 A1 * | 5/2005 | Sabol | A61B 5/055 700/182 |

(Continued)

*Primary Examiner* — Avinash Yentrapati
(74) *Attorney, Agent, or Firm* — Jefferson IP Law, LLP

(57) ABSTRACT

There is provided an apparatus for visualizing a region of interest (ROI) in a Computer Aided Diagnosis (CAD) system. The apparatus includes: an image receiver configured to receive images; an ROI acquirer configured to acquire the ROI from a current image; and an ROI visualizer configured to, in response to acquisition of the ROI from the current image, output visualization information for visualizing the ROI acquired from the current image based on a change between the ROI acquired from the current image and an ROI acquired from a previous image.

18 Claims, 11 Drawing Sheets

(56) References Cited

U.S. PATENT DOCUMENTS

| | | | |
|---|---|---|---|
| 2006/0120581 A1* | 6/2006 | Eck | A61B 6/481 382/128 |
| 2009/0076385 A1 | 3/2009 | Jackson et al. | |
| 2011/0075900 A1* | 3/2011 | Masumoto | G06F 19/321 382/128 |
| 2011/0152687 A1* | 6/2011 | Imura | A61B 8/08 600/443 |
| 2011/0299755 A1* | 12/2011 | Zou | A61B 8/5269 382/131 |
| 2013/0094740 A1* | 4/2013 | Vandenberghe | A61B 6/14 382/131 |
| 2013/0188849 A1* | 7/2013 | Gerig | G06T 11/003 382/131 |
| 2014/0354642 A1* | 12/2014 | Wiemker | G06T 5/50 345/424 |
| 2015/0029464 A1* | 1/2015 | Jayasundera | G06T 7/2053 351/246 |
| 2015/0265241 A1* | 9/2015 | Belt | A61B 8/0833 600/424 |
| 2015/0293026 A1* | 10/2015 | Shin | G06T 7/0016 435/6.11 |
| 2015/0332454 A1* | 11/2015 | Yin | G06T 7/0012 382/131 |
| 2016/0048965 A1* | 2/2016 | Stehle | G06T 7/0016 382/131 |

\* cited by examiner

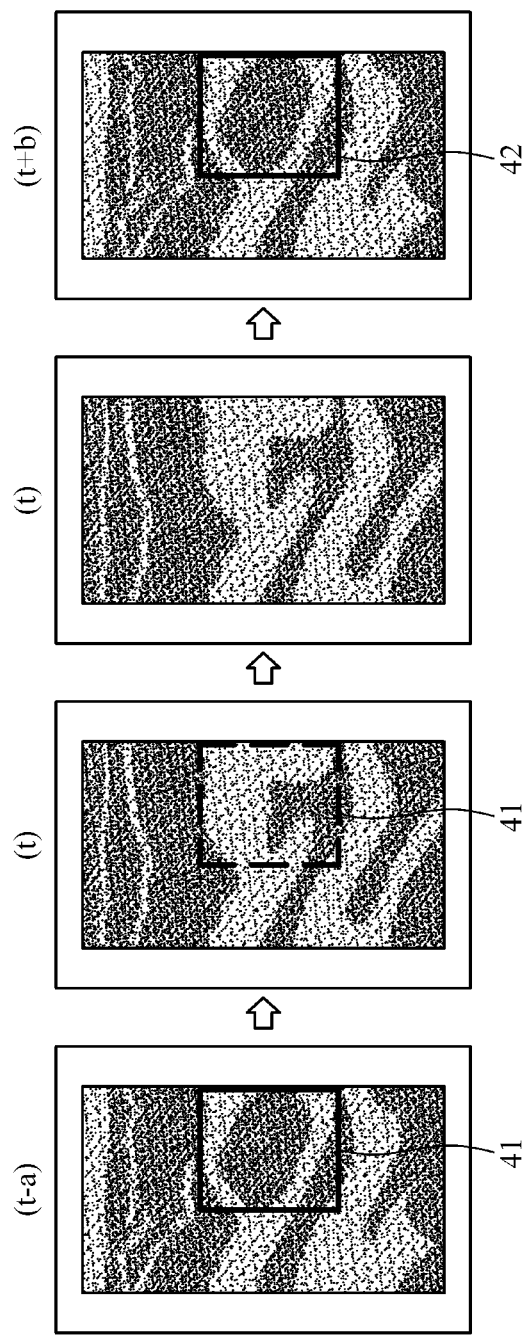

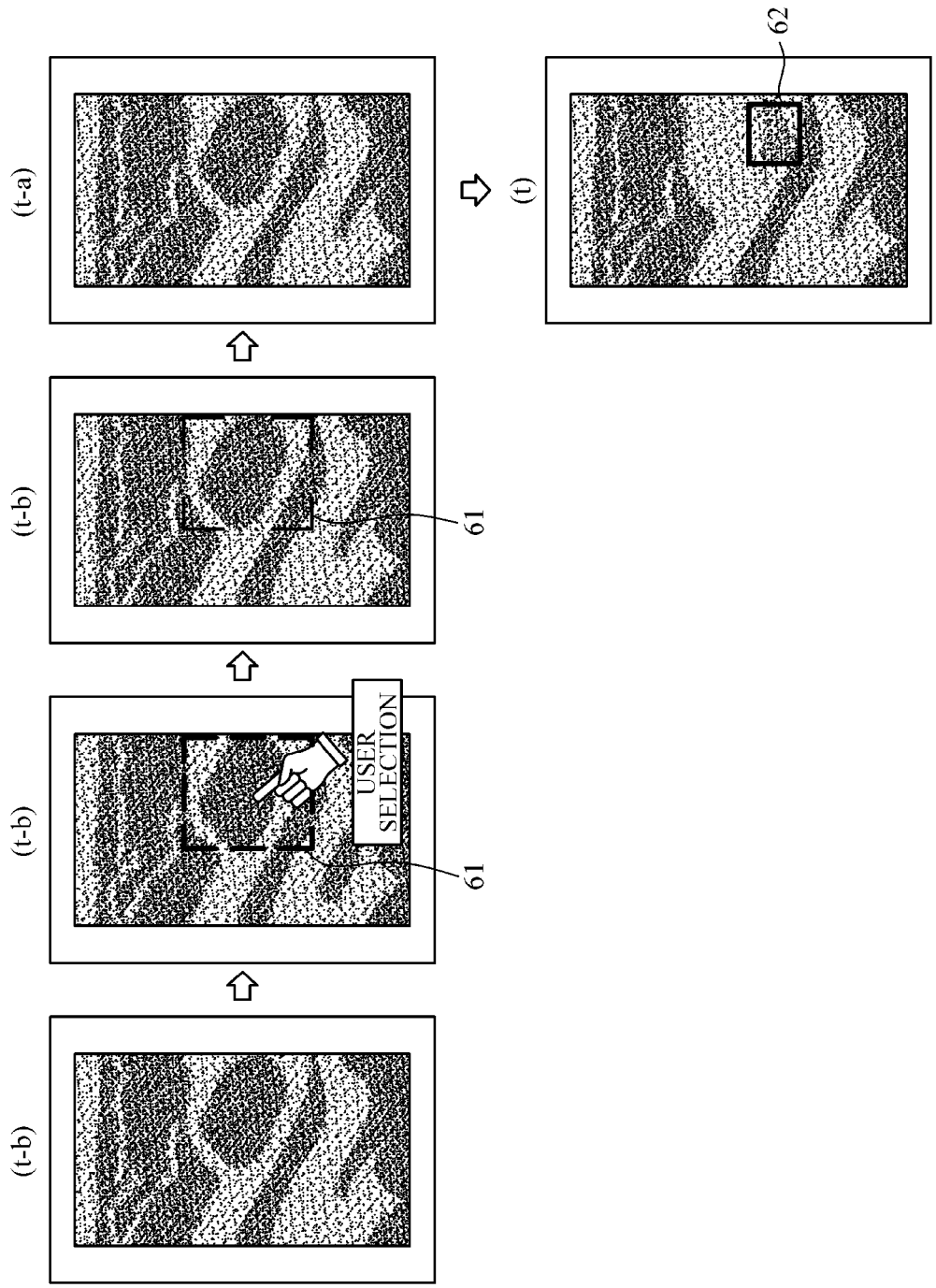

SCAN EXAMINATION AREA FROM TOP TO BOTTOM

SCAN SAME EXAMINATION AREA FROM LEFT TO RIGHT

APPARATUS AND METHOD FOR VISUALIZATION OF REGION OF INTEREST

CROSS-REFERENCE TO RELATED APPLICATION(S)

This application claims the benefit under 35 USC 119(a) of Korean Patent Application No. 10-2014-0100677, filed on Aug. 5, 2014, in the Korean Intellectual Property Office, the entire disclosure of which is incorporated herein by reference for all purposes.

BACKGROUND

1. Field

The following description relates to an apparatus and method of visualizing a region of interest (ROI), and more particularly to a technology using a Computer Aided Diagnosis (CAD) system that is allowed to visualize an ROI.

2. Description of Related Art

In a case of ultrasound examination using an ultrasonic device, such as a fetal ultrasound, an abdominal ultrasound, and a breast ultrasound, both a doctor and a patient look and review a result of the examination on a screen. In general, ultrasonic image diagnosis techniques are designed mainly for measuring a size of a region of interest (ROI) in a still image, visualizing and storing a marking, or displaying and storing an annotation, rather than providing an explanation for patients. Thus, the patients rely on the doctor's explanation to check and understand the result of the ultrasonic examination. However, due to the patient's unfamiliarity with ultrasonic images, it is difficult for the patient to understand which part of an image a doctor is describing and thus the patient may fail to identify the character or significance of the part of the image the doctor is describing. In addition, when a patient requests a more detailed explanation, a doctor needs to take extra actions, for example, the doctor may need to move a probe until the patient can notice a change on an image displayed on the screen, and provide a verbal explanation, or point out an image on the screen using a finger or a pointer.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, there is provided an apparatus of visualizing a region of interest (ROI), the apparatus including: an image receiver configured to receive images; an ROI acquirer configured to acquire the ROI from a current image; and an ROI visualizer configured to, in response to the acquisition of the ROI from the current image, output visualization information for visualizing the ROI acquired from the current image based on a change between the ROI acquired from the current image and an ROI acquired from a previous image.

The ROI acquirer may comprise an ROI detector configured to automatically detect one or more ROIs by applying a detection algorithm to the current image.

The ROI acquirer may comprise an input receiver configured to acquire one or more ROIs from the current image based on an input.

The ROI visualizer may comprise: an interest item identifier configured to, in response to the acquisition of the ROI from the current image, identify whether an interest item exists in the ROI acquired from the current image; and an interest item determiner configured to determine whether the interest item in the current image is identical to an interest item detected from the previous image, when the interest item exists in the ROI acquired from the current image.

The interest item identifier may be further configured to identify whether the interest item exists in the ROI acquired from the current image, by extracting, from the ROI acquired from the current image, features comprising one or more of shape, brightness, texture, and correlation with surrounding areas, and classifying an image pattern of the ROI based on the extracted features.

The interest item determiner may be further configured to, in response to the images received being continuous, determine whether the interest item in the current image is identical to the interest item detected from the previous image based on a difference in the ROI acquired from the current image and the ROI acquired from the previous image.

The interest item determiner may be further configured to, in response to the images received being not continuous, determine whether the interest item in the current image is identical to the interest item detected from the previous image by matching the interest item in the current image with a three-dimensional (3D) object generated for the interest item in the previous image.

The ROI visualizer may comprise: an ROI output configured to output visualization information of the ROI acquired from the current image based on a result obtained by the interest item identifier and a determination made by the interest item determiner.

The ROI output may be further configured to adjust the visualization information based on either or both of a number and a size of interest items, when the interest item exists in the ROI acquired from the current image.

The ROI output may be further configured to, in response to a determination that the interest item in the ROI acquired from the previous image does not exist in the ROI acquired from the current image, remove visualization information of the ROI acquired from the previous image from a screen displaying the ROI.

The ROI output may be further configured to, in response to a determination that the interest item in the current image is identical to the interest item detected in the previous image, output visualization information of the ROI acquired from the previous image as visualization information for visualizing the ROI acquired from the current image.

The ROI output may be further configured to, in response to a determination that the interest item in the current image is not identical to the interest item detected from the previous image, output new visualization information that is distinguishable from visualization information of the ROI acquired from the previous image.

The visualization information may be generated by combining first information, which comprises a square, a circle, a free curve, a cross and an arrow, with second information, which comprises color, a line type, and line thickness.

In another general aspect, there is provided a method of visualizing a region of interest (ROI), the method comprising: receiving images; acquiring the ROI from a current image; and, in response to the acquisition of the ROI from the current image, outputting visualization information for visualizing the ROI acquired from the current image based on a change between the ROI acquired from the current image and an ROI acquired from a previous image.

The acquiring of the ROI may include detecting one or more ROIs based on an input and automatically detecting the one or more ROIs by applying a detection algorithm to the current image.

The method may further include: in response to the acquisition of the ROI from the current image, identifying whether an interest item exits in the ROI acquired from the current image; and determining whether the interest item in the ROI acquired from the current image is identical to an interest item detected from the previous image, when the interest item exists in the ROI acquired from the current image.

The determining of whether the interest item in the ROI acquired from the current image is identical to an interest item from the previous image may include, in a case where the images received are continuous, determining whether the interest item in the current image is identical to the interest item detected from the previous image based on a difference between the ROI acquired from the current image and the ROI acquired from the previous image.

The determining of whether the interest item in the ROI acquired from the current image is identical to an interest item from the previous image may include, in a case where the images received are not continuous, determining whether the interest item in the current image is identical to the interest item detected from the previous image by matching the interest item in the current image with a three-dimensional (3D) object generated for the interest item in the previous image.

The outputting of the visualization information may include adjusting the visualization information based on either or both of a number and a size of interest items and outputting the adjusted visualization information, when the interest item exists in the ROI acquired from the current image.

The outputting of the visualization information may include removing visualization information of the ROI acquired from the previous image from a screen displaying the ROI, when the interest item in the ROI acquired from the previous image does not exist in the ROI acquired from the current image.

The outputting of the visualization information may include, in response to a determination that the interest item in the current image is identical to the interest item detected from the previous image, re-outputting visualization information of the ROI acquired from the previous image as visualization information for visualizing the ROI acquired from the current image.

The outputting of the visualization information may include, in response to a determination that the interest item in the current image is not identical to the interest item detected from the previous image, outputting new visualization information that is distinguishable from visualization information of the ROI acquired from the previous image.

Other features and aspects may be apparent from the following detailed description, the drawings, and the claims.

BRIEF DESCRIPTION OF THE DRAWINGS

FIGS. 4A to 4E are diagrams illustrating examples of visualization of an ROI.

Figure 1:
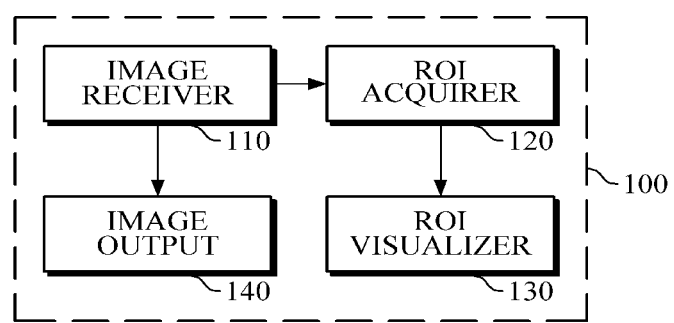
FIG. 1 is a block diagram illustrating an apparatus of visualizing a region of interest (ROI) according to an embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Throughout the drawings and the detailed description, the same reference numerals refer to the same elements. The drawings may not be to scale, and the relative size, proportions, and depiction of elements in the drawings may be exaggerated for clarity, illustration, and convenience.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, an apparatus and method of visualizing a region of interest (ROI) are described with reference to the following drawings.

FIG. 1 is a block diagram illustrating an apparatus of visualizing a region of interest (ROI) according to an embodiment. An apparatus 100 of visualizing an ROI, shown in FIG. 1, may be a component of a Computer-Aided Diagnosis (CAD) system that receives images in sequence and performs a diagnosis on the received image. According to an embodiment, the apparatus 100 may be part of a CAD system that analyzes and diagnoses ultrasonic images received in real time from a probe, as described below. However, aspects of the present disclosure are not limited thereto.

Referring to FIG. 1, the apparatus 100 includes an image receiver 110, an ROI acquirer 120, an ROI visualizer 130, and an image output 140. Although FIG. 1 illustrates the image receiver 110, the ROI acquirer 120, the ROI visualizer 130 and the image output 140 as included in the apparatus 100, these components may be embodied as independent hardware. Therefore, the apparatus 100 illustrated in FIG. 1 is not limited thereto and thus may include more or less components.

The image receiver 110 receives images in sequence. The image receiver 110 may receive images of an examination area of a patient from an image acquiring device in real time. There may be a plurality of image acquiring devices, and an image acquiring device may be an ultrasound examination device that converts a signal of a patient, such as a biological signal, measured by a probe, into an electronic signal and converts the electronic signal into an image. The output electronic signal may change in time, and the image acquiring device may visualize the electronic signal in real time and transmit the visualization result to the image receiver. In addition, according to an embodiment, images received in sequence may be real-time input images in units of frames.

The image output 140 outputs an image received by the image receiver 110. According to an embodiment, if images are received in sequence from the image receiver 110, the image output 140 outputs the current image on a screen, while making a previous image disappear on the screen. According to another embodiment, the image output 140 may output the current image in a predetermined area of the screen, while outputting on a different area of the screen an image that is designated by a user from among previous images as an image that needs to be maintained. The designation may be in response to a result obtained by the interest item identifier 131 and a determination made by the interest item determiner 132. In this case, when a diagnostic result is generated through analysis of a received image, the diagnostic result may be output in a predetermined area of the screen. The diagnostic result may overlay the current image that is already being output on the screen.

If the image receiver 110 receives images in sequence, the ROI acquirer 120 may acquire an ROI from the currently received image according to a predetermined standard, and calculate a location and size of the ROI. The ROI may indicate an area where an interest item exists or is supposed to exist in the image. The interest item may include, for example, a lesion, an embryo, or a fetus finger/toe, but is not limited thereto. In this case, the interest item may be preset according to a diagnostic purpose.

The ROI visualizer 130 visualizes an ROI input by a user or acquired through automatic detection and outputs the ROI on a screen. Once a user designates an ROI in an image output on the screen, the ROI visualizer 130 may visualize the designated ROI by outputting preset visualization information on the screen. In this case, the visualization information may be previously generated by combining first information, which includes, for example, a square, a circle, a free curve, a cross, and an arrow, with second information, which includes, for example, a color, a line type, and line thickness. In addition, according to a type of each interest item and whether each interest item is first detected, the visualization information may be previously combined by a user's input, and then stored.

For example, if a user touches a screen with a finger or a touch pen, the ROI visualizer 130 may visualize an ROI by displaying a cross at the center of the touched point or by displaying a distinguishing marker, such as, for example, a square and/or a circle, on the boundary of an area at a predetermined distance away from the center of the touched point. In addition, if a user draws a boundary of an ROI, the ROI visualizer 130 may output a distinguishing marker on the edge of the touched point by using, for example, various colors, line types, and line thickness, all of which may be preset by a user.

Figure 2:
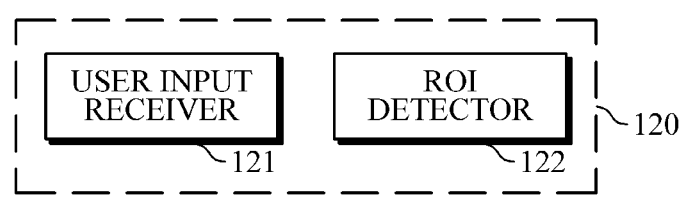
FIG. 2 is a block diagram illustrating an ROI acquirer shown in FIG. 1.

FIG. 2 is a block diagram illustrating an ROI acquirer shown in FIG. 1.

Referring to FIG. 2, the ROI acquirer 120 may include a user input receiver 121 and an ROI detector 122. Although FIG. 2, illustrates the user input receiver 121 and the ROI detector 122 included in the ROI acquirer 120, the user input receiver 121 and the ROI detector 122 may be embodied as independent hardware. Therefore, the ROI acquirer 120 illustrated in FIG. 2 is not limited thereto and thus the ROI acquirer 120 may include more or less components.

The user input receiver 121 receives various types of information that is input by a user using various devices. The various devices may include a probe, a mouse, a touch pen, and a finger. The user input receiver 121 may provide a user interface and may receive various user inputs through the user interface.

According to an embodiment, the user input receiver 121 may receive and set various reference information from a user, which may be necessary for visualization of an ROI. For example, the user input receiver 121 may receive an ROI acquisition condition and a detection algorithm for automatic detection. Herein, the ROI acquisition condition may include 'automatic acquisition,' which indicates automatically detecting an ROI using a detection algorithm, and 'manual acquisition,' which indicates acquiring an ROI based on a user's input. The detection algorithm may include Deformable Parts Model (DPM). In addition, in the case of automatic detection, the reference information may include a threshold of possibility to be an interest item, which may be necessary for acquiring an ROI, and the maximum number of ROIs to be output on the screen.

In addition, the user input receiver 121 may receive and set visualization information from a user in order to visualize the acquired ROI. The visualization information received from the user may include the first information, which indicates a type of distinguishing marker, such as a square, a circle, a free curve and a cross, and the second information, which indicates details of the distinguishing marker, such as a color, a line type, and line thickness. By doing so, the user is able to set and change a distinguishing marker and details thereof.

According to another embodiment, in the case where an ROI acquisition standard is 'manual acquisition', the user input receiver 121 may acquire an ROI by receiving a user's input. If a user designates one or more areas where any interest item is likely to exist in the currently displayed image suspected, the user input receiver 121 may acquire an ROI by calculating a location and size of the area. In this case, the user may designate an ROI of appropriate size according to a size of the interest item by checking the image currently displayed on the screen. That is, the user may designate an ROI by drawing a square, a circle, or a free curve at the boundary of the interest item on the screen. In addition, if the user designates a center of the interest item, the user input receiver 121 may acquire an area of preset-sized area as an ROI by automatically calculating location information of the center of the interest item.

In the case where an ROI acquisition standard is 'automatic acquisition', the ROI detector 122 may automatically detect an ROI by applying a preset detection algorithm to an image each time a new image is received. In this case, the ROI detector 122 detects one or more ROIs from the current image. If a plurality of ROIs are detected, the ROI detector 122 may calculate a possibility of each ROI to include any interest item, and then acquire an area as an ROI if a possibility thereof is greater than a preset threshold (i.e. 50%). In this case, the maximum number of ROIs (e.g., five ROIs) to be output on a screen may be preset according to a resolution of the screen. If the number of ROIs each having a possibility greater than a preset threshold level (e.g., 50%) exceeds the maximum number, the ROI detector 122 may acquire ROIs in descending order of possibilities of ROIs to include any interest item.

Based on a user's input, the user input receiver 121 may acquire an ROI from among the ROIs detected by the ROI detector 122 as an ROI to be constantly traced from among subsequent images. In this case, if visualization information of ROIs automatically detected by the ROI detector is output on a screen, the user may check each ROI and select any area including a desired interest item as an ROI to be traced.

Figure 3:
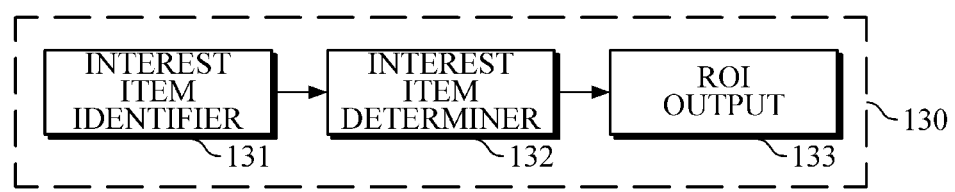
FIG. 3 is a block diagram illustrating an ROI visualizer shown in FIG. 1.

FIG. 3 is a block diagram illustrating an ROI visualizer shown in FIG. 1.

Referring to FIG. 3, the ROI visualizer 130 may include an interest item identifier 131, an interest item determiner 132, and an ROI output 133. Although FIG. 3 illustrates the interest item identifier 131, the interest item determiner 132 and the ROI output 133 included in the ROI visualizer 130, these components may also be embodied as independent hardware. Therefore, the ROI visualizer 130 illustrated in FIG. 3 is not limited thereto and thus the ROI visualizer 130 may include more or less components.

The interest item identifier 131 identifies whether any interest item exists in an ROI acquired by the ROI acquirer 120. The interest item identifier 131 may identify whether any interest item exists in the acquired ROI, by extracting features from the acquired ROI and then classifying an image pattern of the ROI using the extracted features. In this case, the extracted features may include the ROI's shape, brightness, texture, and correlation with surrounding areas.

According to an embodiment, the interest item identifier 131 may utilize a feature extractor and a classifier. Each of the feature extractor and the classifier may be a software program or hardware equipment, and there may be one or more feature extractors/classifiers. In addition, the feature extractor and the classifier may be included in the ROI identifier 131. Alternatively, the feature extractor and the classifier may be included in an additional hardware device or in a CAD device to which the apparatus 100 is utilized.

The feature extractor converts a feature into a numeric value and outputs the numeric value. The output feature consists of a feature vector having numerous values and may be changed according to a received image. To expedite the identifying process, the feature extractor may extract features only from an area of the current image, which has a difference from a previous image. Alternatively, the feature extractor may use the same features as those extracted from a previous image.

The classifier may be a module that is generated by extracting features in each ROI from an image database in advance and performing machine learning on the extracted features. The classifier classifies an image pattern of an ROI by using an image feature vector extracted from the ROI. If an interest item is a lesion, the image pattern may be benign/malignant. According to a type of interest item and a diagnostic purpose, there may be various image patterns. The image pattern may be image patterns.

According to another embodiment, the interest item identifier 131 may identify the existence of an interest item by performing a similarity search to search an image similar to the current image.

If the interest item identifier 131 identifies that any interest item exists in an ROI acquired from the current image, the interest item determiner 132 determines that the identified interest item in the current image includes an interest item detected from a previous image in order to trace the interest item. That is, if an interest item detected from the currently received image is identical to an interest item has been constantly detected from previous images, the interest item determiner 132 continuously traces the interest item and the ROI output 133. The continuously tracing consists of visualizing the ROI in order to notify that the interest item is being traced.

According to an embodiment, based on a degree in change of a received image, the interest item determiner 132 may determine whether the interest item detected from the current image is identical to an interest item detected from a previous image. For example, based on a difference in intensity of ROIs, a difference in histograms, a similarity in histograms, or a difference in a location/angle information of ROIs between the current image and the previous image, the interest item determiner 132 may determine whether the interest items are the same.

According to another embodiment, the interest item determiner 132 may determine whether the interest item detected from the current image is identical to an interest item detected from previous images by matching a three-dimensional (3D) object relating to an ROI acquired from a previous image with a cross-section of the current image.

If a received image is one of images continuously received in real time, the interest item determiner 132 may make a determination based on a degree in change of images. Alternatively, if a received image is a discontinuous image, the interest item determiner 132 may make a determination by matching a 3D object.

In response to a determination that an interest item detected from an ROI in the current image is a new interest item that has not been detected from any previous image, the interest item determiner 132 may process information on the interest item. For example, the interest item determiner 132 may store location and angle information of the newly detected interest item in a storage device, such as a memory and a disc. In addition, each time a new interest item is detected from an image received in sequence, the interest item determiner 132 may generate a 3D object by performing 3D modeling on the new interest item.

At a time when the current image is output on a screen, the ROI output 133 outputs visualization information for visualizing an ROI detected from the current image. That is, if one or more ROIs are detected by a user's input or detected automatically, the ROI output 133 outputs various kinds of visualization information in surroundings of each acquired ROI to notify a user or a patient of the detection of the ROI. If a plurality of ROIs are detected, the ROI output 133 may distinguish the ROIs from each other with different numeric values or colors. For example, the order of numeric values to be output or darkness of a line may be set differently according to a size of ROIs and a possibility of each ROI to include an interest item. For example, in descending order of size of ROIs, 1, 2, 3, . . . , and N may be attached in sequence, red, orange, yellow and blue may be displayed in sequence, or line thickness may gradually become thin. Likewise, the same display method may be applied to the ROIs in descending order of possibilities of the ROIs to include an interest item.

In addition, if a user manually designates an ROI on a screen in a case where the ROI acquisition condition is a manual acquisition, the ROI output 133 may output, on the screen, the designated ROI in a preset form, such as a square, a circle, and a free curve.

If a plurality of ROIs are detected automatically in a case where the ROI acquisition condition is automatic detection, the ROI output 133 outputs visualization information of each detected ROI. Then, if a user selects only some of the detected ROIs, the ROI output 133 may remove visualization information of unselected ROIs to notify that the selected ROIs are to be analyzed and traced. Alternatively, the ROI output 133 may change visualization information of the selected ROIs distinguishably from those of unselected ROIs.

In addition, based on a result obtained by the interest item identifier 131 and a determination made by the interest item determiner 132, the ROI output 133 may output visualization information for visualizing only an ROI detected from the current image.

For example, if the interest item identifier 131 identifies that an interest item exists in an ROI acquired from the current image, the ROI output 133 may adjust visualization information to be output based on the number and size of interest items included in the ROI and may output the adjusted visualization information. That is, as described above, in a case where there are a plurality of interest items, it is possible to output visualization information of an ROI including one interest item distinguishably from that of a different ROI including another interest item. In addition, it is possible to dynamically adjust a size of visualization information of an ROI in proportion to a size of an interest item included therein.

In another example, if the interest item determiner 132 determines that an interest item detected from a previous image exists in the current image, visualization information of the previously detected interest item, which was once output, may be re-output to notify a patient and a doctor that the corresponding interest item was previously detected. New visualization information of each newly detected interest item may be output distinguishably from that of the previously detected interest item to notify the patient and the doctor that a new interest item is detected.

According to the embodiments, visualization information is removed or maintained depending on whether an ROI and/or interest item exists in an ultrasonic image and on whether an interest item was previously detected. In addition, the visualization information of a newly detected interest item is output with a new color, shape, form, or the like, which are distinguishable from those of a previously detected interest item. As a result, a user and a doctor are able to recognize each other's interest items.

FIGS. 4A to 4E are diagrams illustrating examples of visualization of an ROI. Herein, (t) denotes the current point in time. From the current point in time, (t−b) denotes a point in time prior to time b, (t−a) denotes a point in time prior to time a, and (t+b) denotes a point in time after time b. In addition, a point in time may be a unit of frames.

FIG. 4A is an example of ROI visualization in a case where an interest item is a lesion and an ROI is acquired based on the user's input. In FIG. 4A, when the user designates an ROI in surroundings of an interest item in an image received at (t−a) (left image), preset visualization information of a square 41 is accordingly output. At this point, the output square 41 may be output with a particular color, for example, yellow, predetermined by the user from among various colors. Then, if images are received in sequence and the interest item disappears in the image received at (t) (the second and third images from the left), visualization information of the ROI is removed from the screen, as shown in the third image from the left. At this point, it is possible to make the square 41 seem to disappear, not instantly, but gradually by changing the shape of the square 41 (the second image from the left), as shown in the second image from the left, gradually blurring the output color, or changing a type of the line of the square 41. Then, images are received continuously, and, if the interest item designated by the user at (t−a) is re-detected from an image at (t+b) (the image at the right), the square 41, which was output at (t−a), is output again as square 42 at (t+b).

Figure 4B:
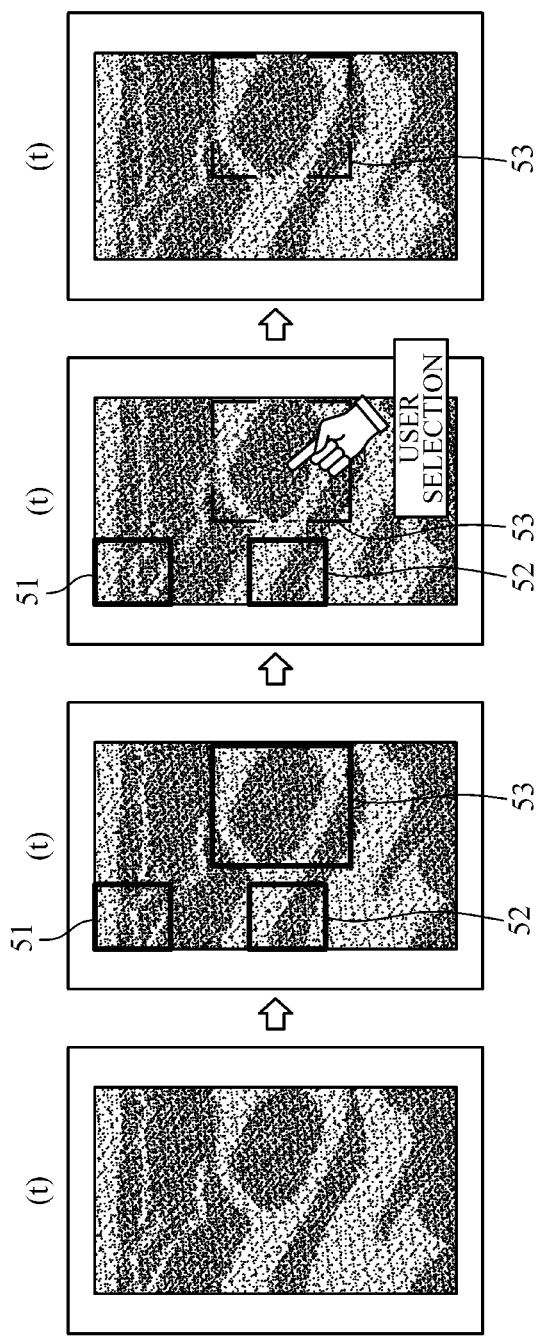

FIG. 4B is another example of ROI visualization in a case where an interest item is a lesion and an ROI is acquired through automatic detection. In FIG. 4B, when an image at (t) (the left image) is received, an ROI is detected from the image through automatic detection, and when three ROIs are acquired as a result, squares 51, 52, and 53 for the respective three ROIs are output on the screen (corresponding to the second image from the left). At this point, size of the squares 51, 52, and 53 may be determined in accordance with a size of the interest item. In addition, the squares 51, 52, and 53 may be output with different types of colors and lines or with the same type of color and line. Then, if a user selects any one of the squares, for example, the square 53, it is possible to notify that the square 53 is the ROI finally selected by the user, by changing a type of color or line of the square 53 (corresponding to the third image from the left) while removing the squares 51 and 52 for the ROIs not selected by the user (corresponding to the image at the right).

FIG. 4C is another example of ROI visualization in a case where an interest item is a lesion and an ROI is acquired based on the user's input. In FIG. 4C, if an image at (t−b) is received and output on a screen (the left image) and a user touches a point suspected to be an ROI, a dotted-line square 61 centered at the touched point is output (corresponding to the second image from the left). Then, in order to notify that the touched point is acquired as an ROI, the dotted-line square 61 may be changed to have a different type of line and/or color and maintained for a while, and then may disappear (corresponding to the third image from the left). Then, images are received continuously and diagnosis is performed (the right image at the bottom). If an interest item first appears in the ROI designated in the image at (t), a square 62 centered at the interest item is output. At this point, the size of the square 62 may be dynamically adjusted in proportion to a size of the interest item.

Figure 4D:
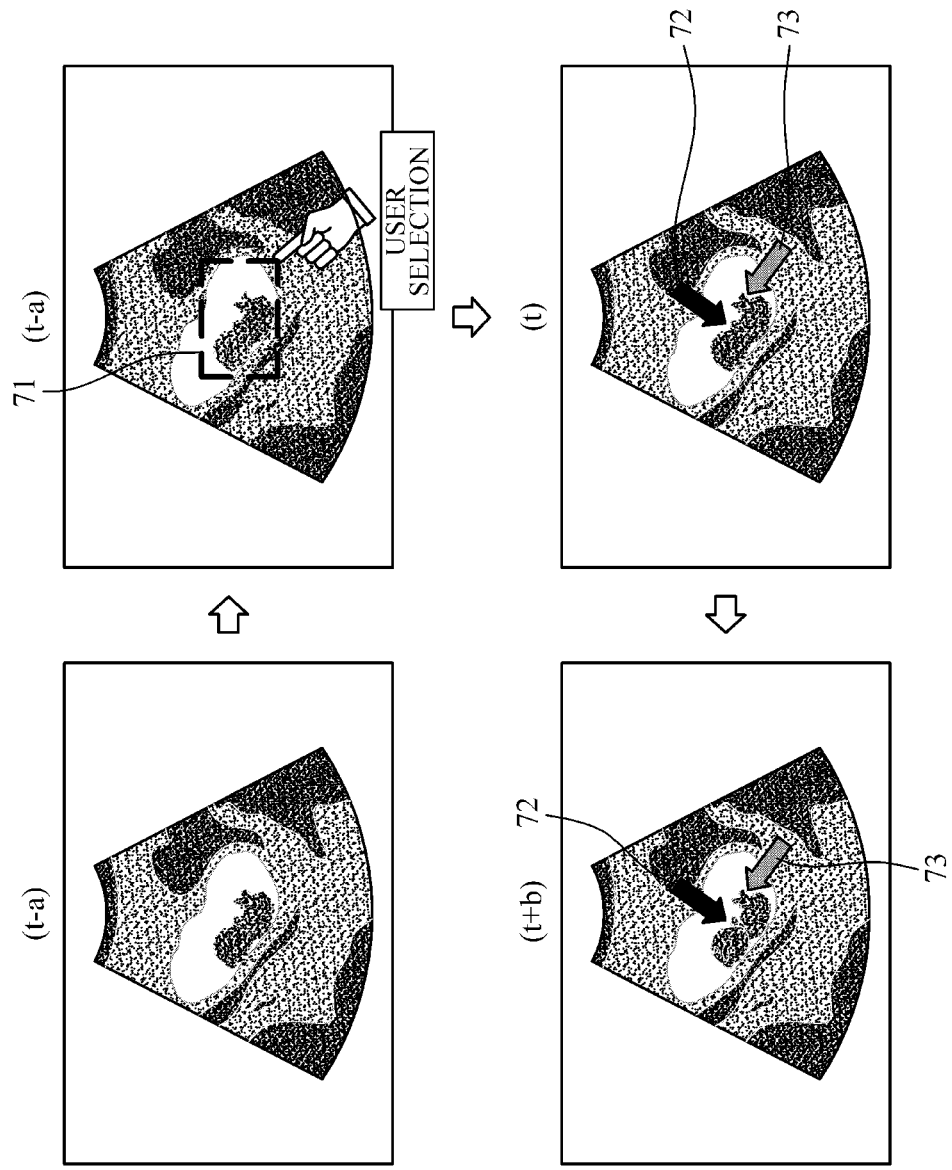

FIG. 4D is another example of ROI visualization in a case where an interest item is a fetus finger or toe and a user designates an ROI in a received image. Likewise, an abdominal ultrasonic image is received and output at (t−a) (corresponding to the left image on the top). If a user designates an area suspected to include a fetus, a dotted-line square 71 is output (corresponding to the right image at the top). Then, if a next image is received, the square 71 disappears and diagnosis on the next image is performed. If a fetal finger and toe is found in the current image received at (t), arrows 72 and 73 of different colors are output (corresponding to the right image at the bottom). Then, if the interest item is continuously detected in subsequent images, the arrows 72 and 73 output with respect to the interest item at (t+b) continues to be output (corresponding to the left image on the bottom). At this point, location and size of an arrow in an image received in real time may be changed according to location and size of the interest item. In addition, if the interest item disappears or appears in the image, the arrows 72 and 73 may thereby disappear or appear.

Figure 4E:
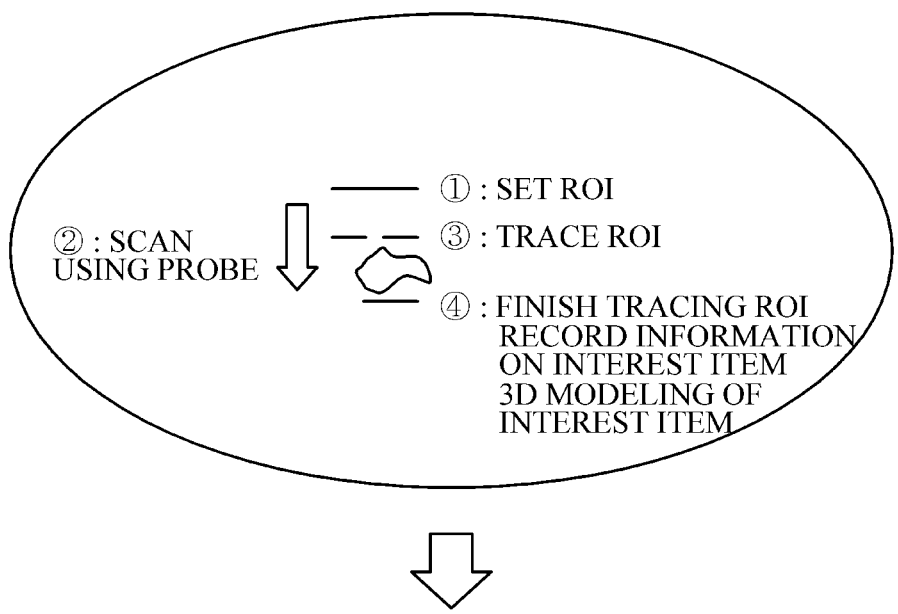
Figure 4E:
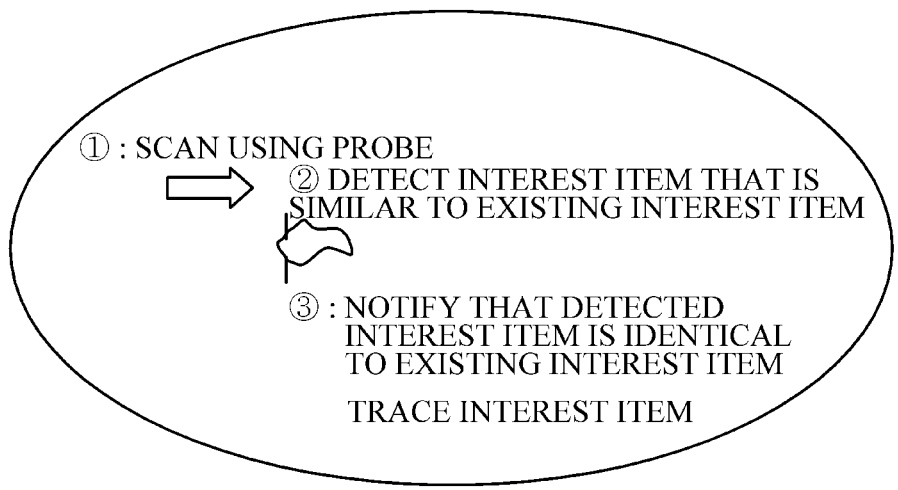

FIG. 4E is another example of ROI visualization in which an ultrasonic image is acquired by scanning the same area of examination with a probe in a different scanning direction. The upper part of FIG. 4E illustrates a procedure in which a user performs diagnosis by scanning an area of examination in a top-to-bottom direction. Specifically, the user sets an ROI (1̂), scans an area of examination in a top-to-bottom direction (2̂), traces the ROI (3̂), stores information on location and size of a detected interest item when the trace is finished, and performs 3D modeling of the interest item to generate a 3D object of the interest item (4̂). That is, an interest item is constantly traced from the point in time when the interest item was first detected from a previous image, and a 3D object of the interest item may be generated by rendering volume information of the interest item.

The lower part of FIG. 4E illustrates a procedure where a user performs diagnosis by scanning the same area of examination in a left-to-right direction. A user acquires a real-time image by moving a probe from the left side to the right side ($\hat{1}$), and, in response to an interest item found at a location from an arbitrary distance from the previously detected interest item in the upper side, matches the interest item with the previously generated 3D object in order to determine whether the interest item is identical to the previously detected interest item ($\hat{2}$). If a determination is made that the interest item is identical or similar to the previously detected interest item, visualization information, which was once output for the previously detected interest item, is output again, and the interest item may be traced ($\hat{3}$).

Figure 5:
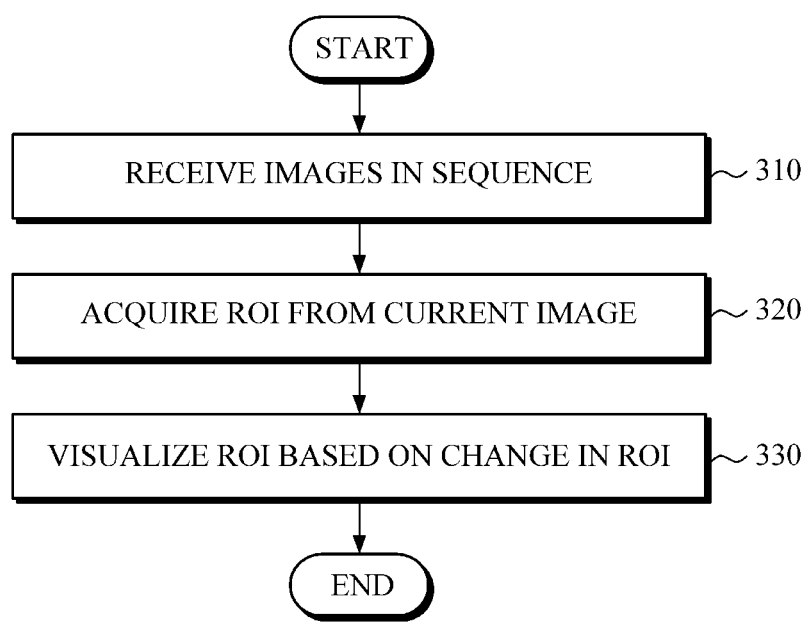
FIG. 5 is a flowchart illustrating a method of visualizing an ROI according to an embodiment.
Figure 6:
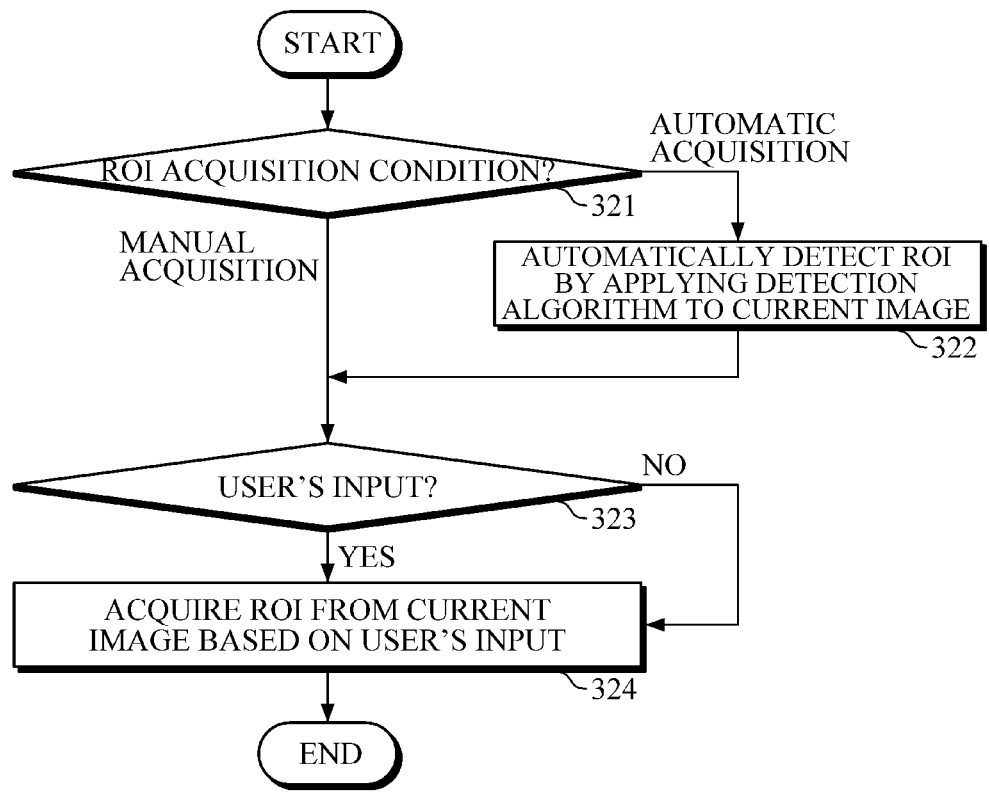
FIG. 6 is a flowchart illustrating an ROI acquiring operation shown in FIG. 5.
Figure 7:
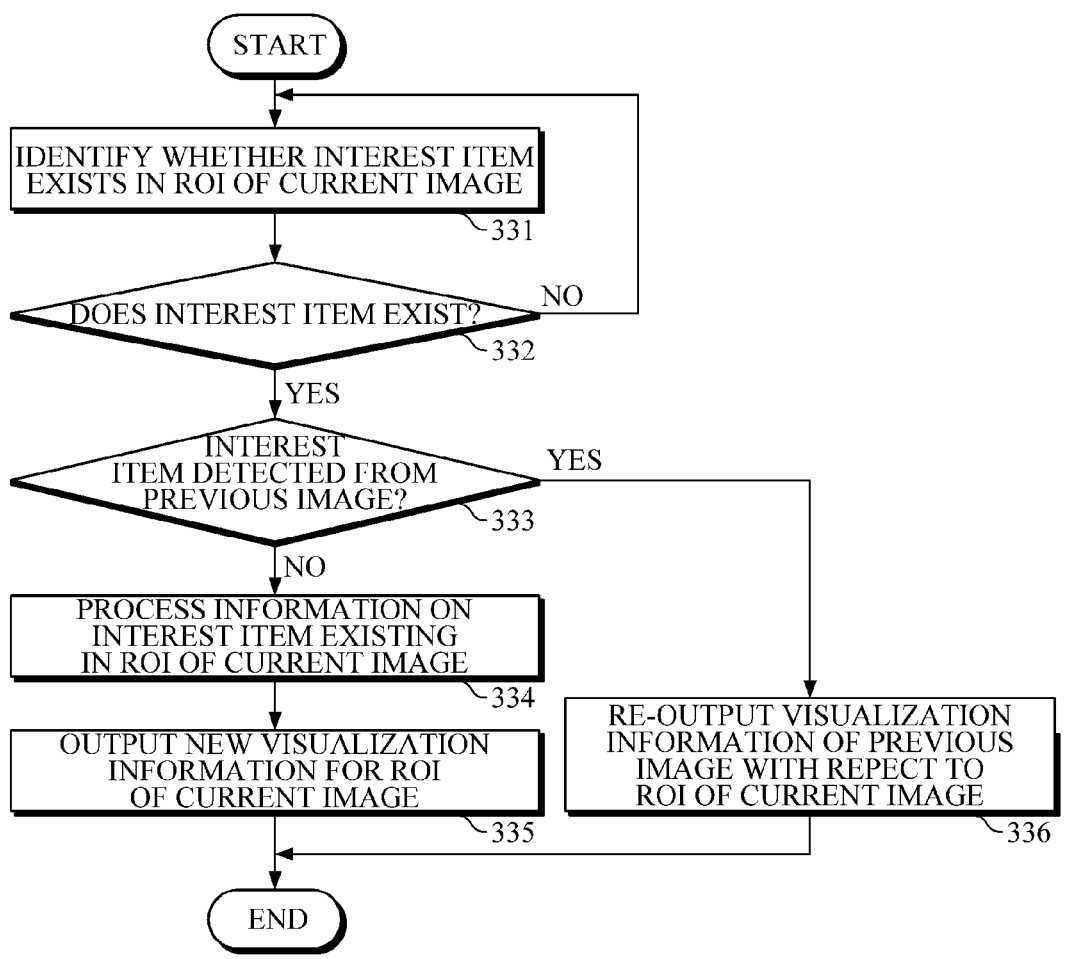
FIG. 7 is a flowchart illustrating an ROI visualizing operation shown in FIG. 5.

FIG. 5 is a flowchart of a method of visualizing an ROI according to an embodiment. FIG. 6 is a flowchart illustrating an ROI acquiring operation shown in FIG. 5. FIG. 7 is a flowchart illustrating an ROI visualizing operation shown in FIG. 5.

FIGS. 5 to 7 may be examples of a method of visualizing an ROI by the apparatus shown in the embodiment of FIG. 1. Since various embodiments have been already described in detail, descriptions thereof are hereinafter omitted.

In operation 310, the apparatus 100 receives images in sequence. The images received in sequence may be ultrasonic images in units of frames, which are acquired in real time by a probe.

In operation 320, the apparatus 100 acquires an ROI from the currently received image. At this point, the ROI may be acquired automatically or manually based on a user's input.

Referring to FIG. 6, operation 320 is described in detail. In operation 321, the apparatus 100 checks a preset ROI acquisition condition. The ROI acquisition condition may be preset by a user, and may include automatic detection and manual detection. In the case of automatic detection, it is possible to set a detection algorithm, a threshold for possibility of each ROI to include an interest item, and the maximum number of ROIs to be output.

If it is found in operation 321 that the preset ROI acquisition condition is automatic detection, a detection algorithm is applied to the currently received image to detect one or more ROIs in operation 322. The one or more detected ROIs are output with various types of visualization information, as described below.

Then, if a user inputs selection of a desired ROI in operation 323 after checking visualization information of each ROI on the screen, the apparatus 100 may acquire the selected ROI as an ROI to be traced in operation 324. At this point, if user does input selection of none or all of the detected ROIs, the apparatus 100 may acquire an automatically detected ROI as an ROI to be diagnosed and traced.

Alternatively, if it is found in operation 321 that the ROI acquisition condition is manual detection, the apparatus 100 waits to receive a user's input. If the user identifies an interest item and designates an ROI in the current image in operation 323, the apparatus 100 acquires the designated ROI as an ROI to be diagnosed and traced in operation 324. At this point, the user may designate an ROI using various inputting methods. For example, the user may designate an ROI by touching the center of an area suspected to include any interest item or by drawing a square, a circle, or a free curve around the suspected area.

Again referring to FIG. 5, if an ROI is acquired from the currently received image, the apparatus 100 visualizes the ROI in operation 330. Specifically, if the ROI is acquired based on a user's input or through automatic detection, the apparatus 100 may output, on the edge of the ROI, visualization information such as a square, a free curve, an arrow and a cross of various colors, line types, and line thickness.

Referring to FIG. 7, operation 330 of visualizing an ROI is described in more detail. In operation 331, whether any interest item exists in an ROI of the current image is identified. In a case where it is found in operation 322 that any interest item does not exists in an ROI of the current image, whether any interest item exists in an ROI of a subsequent image is identified in operation 331. Whether any interest item exists in an ROI may be identified by extracting features from the current image and classifying an image pattern based on the extracted features.

If it is found in operation 332 that an interest item exists in the ROI acquired from the current image, whether the interest item in the current image is identical to an interest item detected from a previous image is determined in operation 333. If received images are continuous images input in real time, whether the interest item in the current image is identical to an interest item detected from a previous image may be determined based on a change between the ROI acquired from the current image and an ROI acquired from the previous image. Alternatively, if the received image is a discontinuous image, i.e., an image scanned in a different direction of the same area, whether the interest item in the current image is identical to an interest item detected from a previous image may be determined by matching the interest item in the current image with a 3D object previously generated for the interest item in a previous image.

If it is determined in operation 333 that the interest item is not identical to the interest item detected from the previous image, information on the interest item is processed in operation 334. For example, information of a newly detected interest item, such as location and size thereof, is recorded and managed in a storage device, and 3D modeling of the newly detected interest item is performed to generate a 3D object. In addition, the newly detected interest item or an ROI including the same is output in operation 335 to notify a user of the detection.

If it is determined in operation 333 that the interest item is identical to an interest item detected from a previous image, visualization information that was output regarding the previous image is output again with respect to an ROI in the current image in operation 336.

The methods and/or operations described above may be recorded, stored, or fixed in one or more non-transitory computer-readable storage media that includes program instructions to be implemented by a computer to cause a processor to execute or perform the program instructions. The non-transitory computer-readable storage media may also include, alone or in combination with the program instructions, data files, data structures, and the like. Examples of non-transitory computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules in order to perform the operations and methods described above, or vice versa. In addition, a non-transitory computer-readable storage medium may be distributed among computer systems connected through a network and computer-readable codes or program instructions may be stored and executed in a decentralized manner.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus to visualize a region of interest (ROI), comprising:
   at least one processor; and
   at least one memory storing one or more computer programs that, upon execution by the at least one processor, configure the at least one processor to:
      receive images in sequence via a probe,
      acquire at least one ROI comprising at least one pre-designated interest item from one (hereinafter, previous image) among the images,
      output visualization information for visualizing the at least one ROI acquired from the previous image on the previous image,
      detect at least one ROI from a current image received by a movement of the probe,
      identify, in response to detection of the at least one ROI from the current image, whether an interest item exists in the at least one ROI detected from the current image,
      remove, in response to a determination that the interest item does not exist in the at least one ROI detected from the current image, the visualization information of the at least one ROI acquired from the previous image,
      determine, in response to a determination that the interest item exists in the at least one ROI detected from the current image, whether the interest item existing in the current image is identical to the pre-designated interest item in the previous image, and
      output the visualization information of the at least one ROI acquired from the previous image as visualization information for visualizing the at least one ROI detected from the current image on the current image based on a result of the determination.

2. The apparatus of claim 1, wherein the at least one processor is further configured to:
   automatically acquire one or more ROIs by applying a detection algorithm to the previous image.

3. The apparatus of claim 1, wherein the at least one processor is further configured to:
   acquire one or more ROIs from the previous image based on a user's input.

4. The apparatus of claim 1, wherein the at least one processor is further configured to:
   identify whether the interest item exists in the ROI detected from the current image, by extracting, from the at least one ROI detected from the current image, features comprising one or more of shape, brightness, texture, and correlation with surrounding areas, and classifying an image pattern of the at least one ROI based on the extracted features.

5. The apparatus of claim 1, wherein the at least one processor is further configured to:
   determine, in response to the images received in sequence being continuous, whether the interest item existing in the current image is identical to the pre-designated interest item in the previous image based on a difference in the at least one ROI detected from the current image and the at least one ROI acquired from the previous image.

6. The apparatus of claim 1, wherein the at least one processor is further configured to:
   determine, in response to the images received in sequence being not continuous, whether the interest item existing in the current image is identical to the pre-designated interest item in the previous image by matching the interest item existing in the current image with a three-dimensional (3D) object generated for the pre-designated interest item in the previous image.

7. The apparatus of claim 1, wherein the at least one processor is further configured to:
   adjust the visualization information of the at least one ROI acquired from the previous image based on either or both a number and size of interest items, when the interest item exists in the at least one ROI detected from the current image, and
   output the adjusted visualization information as the visualization information for visualizing the at least one ROI detected from the current image.

8. The apparatus of claim 1, wherein the at least one processor is further configured to:
   output, in response to a determination that the interest item existing in the current image is identical to the pre-designated interest item in the previous image, the visualization information of the at least one ROI acquired from the previous image as the visualization information for visualizing the at least one ROI detected from the current image on the current image.

9. The apparatus of claim 1, wherein the at least one processor is further configured to:
   output, in response to a determination that the interest item existing in the current image is not identical to the pre-designated interest item in the previous image, new visualization information that is distinguishable from the visualization information of the at least one ROI acquired from the previous image as the visualization information for visualizing the at least one ROI detected from the current image on the current image.

10. The apparatus of claim 1, wherein the visualization information is generated by combining first information, which comprises a square, a circle, a free curve, a cross and an arrow, with second information, which comprises color, a line type, and line thickness.

11. A method of visualizing a region of interest (ROI), comprising:
   receiving images in sequence via a probe;
   acquiring at least one ROI comprising at least one pre-designated interest item from one (hereinafter, previous image) among the received images;
   outputting visualization information for visualizing the at least one ROI acquired from the previous image on the previous image;
   detecting at least one ROI from a current image received by a movement of the probe;
   identifying, in response to detection of the at least one ROI from the current image, whether an interest item exists in the at least one ROI detected from the current image;

removing, in response to a determination that the interest item does not exist in the at least one ROI detected from the current image, the visualization information of the at least one ROI acquired from the previous image;

determining, in response to a determination that the interest item exists in the at least one ROI detected from the current image, whether the interest item existing in the current image is identical to the pre-designated interest item in the previous image; and outputting the visualization information of the at least one ROI acquired from the previous image as visualization information for visualizing the at least one ROI detected from the current image on the current image based on a result of the determination.

12. The method of claim 11, wherein the acquiring of the at least one ROI comprises one of:

acquiring one or more ROIs based on a user's input; or automatically acquiring one or more ROIs by applying a detection algorithm to the previous image.

13. The method of claim 11, wherein the determining comprises, in a case where the images received in sequence are continuous, determining whether the interest item existing in the current image is identical to the pre-designated interest item in the previous image based on a difference between the at least one ROI detected from the current image and the at least one ROI acquired from the previous image.

14. The method of claim 11, wherein the determining comprises, in a case where the image received in sequence are not continuous, determining whether the interest item existing in the current image is identical to the pre-designated interest item in the previous image by matching the interest item existing in the current image with a three-dimensional (3D) object generated for the pre-designated interest item in the previous image.

15. The method of claim 11, wherein the outputting of the visualization information for visualizing the at least one ROI detected from the current image comprises:

adjusting, when the interest item exists in the at least one ROI detected from the current image, the visualization information of the at least one ROI acquired from the previous image based on either or both a number and size of interest items; and outputting the adjusted visualization information as the visualization information for visualizing the at least one ROI detected from the current image.

16. The method of claim 11, wherein the outputting of the visualization information for visualizing the at least one ROI detected from the current image comprises, in response to a determination that the interest item existing in the current image is identical to the pre-designated interest item in the previous image, re-outputting the visualization information of the at least one ROI acquired from the previous image as the visualization information for visualizing the at least one ROI detected from the current image on the current image.

17. The method of claim 11, wherein the outputting of the visualization information for visualizing the at least one ROI detected from the current image comprises, in response to determination that the interest item existing in the current image is not identical to the pre-designated interest item in the previous image, outputting new visualization information that is distinguishable from the visualization information of the at least one ROI acquired from the previous image as the visualization information for visualizing the at least one ROI detected from the current image on the current image.

18. A computer program product comprising a non-transitory computer readable storage medium having a computer readable program stored therein, wherein the computer readable program, when executed on a computing device, causes the computing device to:

receive images in sequence, acquire at least one ROI comprising at least one pre-designated interest item from one (hereinafter, previous image) among the images, output visualization information for visualizing the at least one ROI acquired from the previous image on the previous image, detect at least one ROI from a current image received by a movement of the probe, identify, in response to detection of the at least one ROI from the current image, whether an interest item exists in the at least one ROI detected from the current image, remove, in response to a determination that the interest item does not exist in the at least one ROI detected from the current image, the visualization information of the at least one ROI acquired from the previous image, determine, in response to a determination that the interest item exists in the at least one ROI detected from the current image, whether the interest item existing in the current image is identical to the pre-designated interest item in the previous image, and output the visualization information of the at least one ROI acquired from the previous image as visualization information for visualizing the at least one ROI detected from the current image on the current image based on a result of the determination.

* * * * *